(12) United States Patent
Hangeland

(10) Patent No.: US 6,831,102 B2
(45) Date of Patent: Dec. 14, 2004

(54) PHENYL NAPHTHOL LIGANDS FOR THYROID HORMONE RECEPTOR

(75) Inventor: Jon J. Hangeland, Morrisville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 61 days.

(21) Appl. No.: 10/313,864

(22) Filed: Dec. 6, 2002

(65) Prior Publication Data

US 2003/0166724 A1 Sep. 4, 2003

Related U.S. Application Data

(60) Provisional application No. 60/337,760, filed on Dec. 7, 2001.

(51) Int. Cl.⁷ .................. A01N 37/10; A01N 37/12; A01N 37/44; A61K 31/235; A61K 31/24
(52) U.S. Cl. .................. 514/532; 514/534; 514/535; 514/563; 514/569; 560/27; 560/29; 560/30; 560/45; 560/47; 560/48; 562/455; 562/456; 562/457
(58) Field of Search ................ 514/532, 534, 514/535, 563, 569; 560/27, 29, 30, 45, 47, 48; 562/455, 456, 457, 558

(56) References Cited

U.S. PATENT DOCUMENTS

| | | | |
|---|---|---|---|
| 3,239,345 A | 3/1966 | Hodge et al. | 99/2 |
| 3,864,146 A * | 2/1975 | Oda et al. | 117/36.8 |
| 3,865,848 A | 2/1975 | Nysted | 260/346.1 |
| 3,983,140 A | 9/1976 | Endo et al. | 260/343.5 |
| 4,027,009 A | 5/1977 | Grier et al. | 424/78 |
| 4,036,979 A | 7/1977 | Asato | 424/275 |
| 4,231,938 A | 11/1980 | Monaghan et al. | 260/343.5 |
| 4,346,227 A | 8/1982 | Terahara et al. | 560/119 |
| 4,411,890 A | 10/1983 | Momany | 424/177 |
| 4,448,784 A | 5/1984 | Glamkowski et al. | 424/274 |
| 4,450,171 A | 5/1984 | Hoffman et al. | 424/279 |
| 4,499,289 A | 2/1985 | Baran et al. | 549/292 |
| 4,613,610 A | 9/1986 | Wareing | 514/406 |
| 4,647,576 A | 3/1987 | Hoefle et al. | 514/422 |
| 4,681,893 A | 7/1987 | Roth | 514/422 |
| 4,686,237 A | 8/1987 | Anderson | 514/532 |
| 4,759,923 A | 7/1988 | Buntin et al. | 424/440 |
| 4,871,721 A | 10/1989 | Biller | 514/102 |
| 4,924,024 A | 5/1990 | Biller | 558/202 |
| 5,006,530 A | 4/1991 | Angerbauer et al. | 514/277 |
| 5,177,080 A | 1/1993 | Angerbauer et al. | 514/277 |
| 5,273,995 A | 12/1993 | Roth | 514/422 |
| 5,354,772 A | 10/1994 | Kathawala | 514/414 |

(List continued on next page.)

FOREIGN PATENT DOCUMENTS

| | | |
|---|---|---|
| EP | 0142146 | 5/1985 |
| EP | 0221025 | 5/1987 |
| FR | 2596393 | 10/1987 |
| WO | WO 86/03488 | 6/1986 |
| WO | WO 86/07054 | 12/1986 |
| WO | WO 89/07110 | 8/1989 |
| WO | WO 89/07111 | 8/1989 |
| WO | WO 93/04081 | 3/1993 |
| WO | WO 97/21993 | 6/1997 |
| WO | WO 98/09964 | 3/1998 |
| WO | WO 99/00353 | 1/1999 |
| WO | WO 00/01389 | 1/2000 |

OTHER PUBLICATIONS

Anton, U. et al., "Synthesis of n–Alkyl–Substituted Perylenese and Terrylenes via Alkali–Metal Induced Cyclization of Oligonaphthylenes", Chem. Ber., vol. 125, pp. 2325–2330 (1992).

Anton, U. et al., "The Stereochemistry of the Trinaphthyl–Terrylene Conversion", Chem. Ber., vol. 126, pp. 517–521 (1993).

Biller, S.A. et al., "Isopreniod (Phosphinylmethyl)phosphonates as Inhibitors of Squalene Synthetase", Journal of Medicinal Chemistry, vol. 31, No. 10, pp. 1869–1871 (1988).

(List continued on next page.)

Primary Examiner—Richard L. Raymond
Assistant Examiner—Zachary C. Tucker
(74) Attorney, Agent, or Firm—Jonathan N. Provoost; Maureen P. O'Brien

(57) ABSTRACT

New thyroid receptor ligands are provided which have the general formula I:

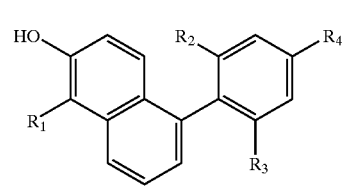

wherein $R_1$ is halogen, trifluoromethyl, substituted or unsubstituted aryl, substituted or unsubstituted $C_{1-6}$ alkyl, or substituted or unsubstituted $C_{3-7}$ cycloalkyl;

$R_2$ and $R_3$ are each independently hydrogen, halogen, substituted or unsubstituted $C_{1-4}$ alkyl, or substituted or unsubstituted $C_{3-6}$ cycloalkyl, wherein at least one of $R_2$ and $R_3$ is other than hydrogen;

$R_4$ is a carboxylic acid selected from the group consisting of $(CH_2)_n COOH$, $(CH)_2 COOH$, $NHCO(CH_2)_n COOH$, $CONH(CH_2)_n COOH$ and $NH(CH_2)_m COOH$;

n is an integer from 0 to 4; and
m is an integer from 1 to 4.

In addition, a method is provided for preventing, inhibiting or treating a disease associated with metabolism dysfunction or which is dependent upon the expression of a $T_3$ regulated gene, wherein a compound as described above is administered in a therapeutically effective amount.

7 Claims, No Drawings

U.S. PATENT DOCUMENTS

| | | | |
|---|---|---|---|
| 5,385,929 A | 1/1995 | Bjorge et al. | 514/422 |
| 5,488,064 A | 1/1996 | Sher | 514/465 |
| 5,491,134 A | 2/1996 | Sher et al. | 514/114 |
| 5,541,204 A | 7/1996 | Sher et al. | 514/359 |
| 5,595,872 A | 1/1997 | Wetterau, II et al. | 435/6 |
| 5,612,359 A | 3/1997 | Murugesan | 514/365 |
| 5,686,104 A | 11/1997 | Mills et al. | 424/451 |
| 5,712,279 A | 1/1998 | Biller et al. | 514/252 |
| 5,712,396 A | 1/1998 | Magnin et al. | 546/22 |
| 5,739,135 A | 4/1998 | Biller et al. | 514/252 |
| 5,760,246 A | 6/1998 | Biller et al. | 548/309.7 |
| 5,770,615 A | 6/1998 | Cheng et al. | 514/365 |
| 5,776,983 A | 7/1998 | Washburn et al. | 514/605 |
| 5,827,875 A | 10/1998 | Dickson, Jr. et al. | 514/424 |
| 5,885,983 A | 3/1999 | Biller et al. | 514/210 |
| 5,962,440 A | 10/1999 | Sulsky | 514/105 |
| 6,043,265 A | 3/2000 | Murugesan et al. | 514/374 |
| 6,184,231 B1 | 2/2001 | Hewawasam et al. | 514/312 |

OTHER PUBLICATIONS

Biller, S.A. et al., "Squalene Synthase Inhibitors", Current Pharmaceutical Design, vol. 2, pp. 1–40 (1996).

Blettner, C.G. et al., "Microwave–Assisted Aqueous Suzuki Cross–Coupling Reactions", J. Org. Chem., vol. 64, pp. 3885–3890 (1999).

Bundgaard, H., Design of Prodrugs, Elsevier Science Publishers B.V. (1985) (table of contents).

Bundgaard, H., "Design and Application of Prodrugs", A Textbook of Drug Design and Development, Harwood Academic Publishers, Krogsgaard–Larsen, P. and Bundgaard, T., eds., pp. 113–191 (1991).

Capson, T.L., "Synthesis and Evaluation of Ammonium Analogs of Carbocationic Intermediates in Squalene Biosynthesis", dissertation, Department of Medicinal Chemistry, University of Utah, pp. iv–v, table of contents, 16–17, 40–43, 48–51 (Jun. 1987).

Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", J. Am. Chem. Soc., vol. 98, No. 5, pp. 1291–1293 (1976).

Edwards, J.P. et al., "Nonsterodial Androgen Receptor Agonists Based on 4–(trifluoromethyl)–2H–pyrano[3,2–g]quinolin–2–one", Bioorganic & Medicinal Chemistry Letters, vol. 9, pp. 1003–1008 (1999).

Frahn, J. et al., "Functionalized AB–Type Monomers for Suzuki Polycondensation", Synthesis, vol. 11, pp. 1301–1304 (1997).

Ghiselli, G., "The Pharmacological Profile of FCE 27677: A Novel ACAT Ihibitor with Potent Hypolipidemic Activity Mediated by Selective Suppression of the Hepatic Secretion of ApoB–100–Containing Lipoprotein", Cardiovascular Drug Reviews, vol. 16, No. 1, pp. 16–30 (1998).

Greene, T.W. et al., Protective Groups in Organic Synthesis, Third Edition, John Wiley & Sons, Inc. (1999) (table of contents).

Hamann, L.G. et al., "Discovery of a Potent, Orally Active, Nonsteroidal Androgen Receptor Agonist: 4–Ethyl–1,2,3,4–tetrahydro–6–(trifluoromethyl)–8–pyridono[5,6–g]–quinoline (LG121071)", J. Med. Chem., vol. 42, pp. 210–212 (1999).

Harada, T. et al., "Asymmetric Synthesis of 6,6α–Dialkyl and –Diphenyl–2,2'–Biphenydiols by Using Menthone as a Chiral Template", Synlett, vol. 3, pp. 283–284 (1995).

Hoye, T.R. et al., "Studies of Palladium–Catalyzed Cross–Coupling Reactions for Preparation of Highly Hindered Biaryls Relevant to the Korupensamine/Michellamine Problem", J. Org. Chem., vol. 61, pp. 7940–7942 (1996).

Hoye, T.R. et al., "Total Syntheses of Korupensamine C and Ancistrobrevine B", Tetrahedron Letters, vol. 37, No. 18, pp. 3097–3098 (1996).

Ishiyama, T. et al., "Palladium(0)–Catalyzed Cross–Coupling Reaction of Alkoxydiboron with Haloarenes: A Direct Procedure for Arylboronic Esters", J. Org. Chem., vol. 60, pp. 7508–7510 (1995).

Johannson, G. et al., "Growth Hormone Treatment of Abdominally Obese Men Reduces Abdominal Fat Mass, Improves Glucose and Lipoprotein Metabolism, and Reduces Diastolic Blood Pressure", J. Clin. Endocrinol. Metab., vol. 82, No. 3, pp. 727–734 (1997).

Kasturi, T.R. et al., "Studies in dehydrogenation of 6–methoxy–1–tetralone. Structure of a novel product formed with tetrachloro–1,2–benzoquinone", Canadian Journal of Chemistry, vol. 46, pp. 3625–3629 (1968).

Krause, B.R. et al., "ACAT Inhibitors: Physiologic Mechanisms for Hypolipidemic and Anti–Atherosclerotic Activities in Experimental Animals", Inflammation: Mediators Pathways, CRC Press, Inc., Ruffolo, Jr., R.R. and Hollinger, M.A., eds., pp. 173–198 (1995).

Kumar, S., "A New and Concise Synthesis of 3–Hydroxybenzo[c]phenanthrene and 12–Hydroxybenzo[g]chrysene, Useful Intermediates for the Synthesis of Fjord–Region Diol Epoxides of Benzo[c]phenanthrene and Benzo[g]chrysene", J. Org. Chem., vol. 62, pp. 8535–8539 (1997).

Matsubara, S. et al., "Methylenation of Carbonyl Compounds by Means of Nysted Reagent", Synlett, vol. 3, pp. 313–315 (1998).

McClard, R.W. et al., "Novel Phosphonylphosphinyl (P–C–P–C–) Analogues of Biochemically Interesting Diphosphates. Syntheses and Properties of P–C–P–C– Analogues of Isopentenyl Diphosphate and Dimethylallyl Diphosphate", J. Am. Chem. Soc., vol. 109, pp. 5544–5545 (1987).

Murata, M. et al., "Novel Palladium (0)–Catalyzed Coupling Reaction of Dialkoxyborane with Aryl Halides: Convenient Synthetic Route to Arylboronates", J. Org. Chem., vol. 62, pp. 6458–6459 (1997).

Nakano, Y. et al., "Synthesis of 5–Substituted Quinolin–8–ois", Synthesis, vol. 12, pp. 1425–1428 (1997).

Nicolosi, R.J. et al., "The ACAT Inhibitor, CI–1011 is effective in the prevention and regression of aortic fatty streak area in hamsters", Atherosclerosis, vol. 137, pp. 77–85 (1998).

Ortiz de Montellano, P.R. et al., "Inhibition of Squalene Synthetase by Farnesyl Pyrophosphate Analogues", Journal of Medicinal Chemistry, vol. 20, No. 2, pp. 243–249 (1977).

Piettre, S.R. et al., "A New Approach to the Solid–Phase Suzuki Coupling Reaction", Tetrahedron Letters, vol. 38, No. 7, pp. 1197–1200 (1997).

Rosenblum, S.B. et al., "Discovery of 1–(4–Fluorophenyl)–(3R)–[3–(4–fluorophenyl)–(3S)–hydroxypropl]–(4S)–(4–hydroxyphenyl)–2–azetidinone (SCH 58235): A Designed, Potent, Orally Active Inhibitor of Cholesterol Absorption", J. Med. Chem., vol. 41, pp. 973–980 (1998).

Salisbury, B.G. et al., "Hypocholesterolemic activity of a novel inhibitor of cholesterol absorption, SCH 48461", Atherosclerosis, vol. 115, pp. 45–63 (1995).

Shieh, W.–C. et al., "A Simple Asymmetric Synthesis of 4–Arylphenylalanines via Palladium–Catalyzed Cross–Coupling Reaction of Arylboronic Acids with Tyrosine Triflate", J. Org. Chem., vol. 57, pp. 379–381 (1992).

Sliskovic, D.R. et al., "ACAT Inhibitors: Potential Anti–atherosclerotic Agents", Current Medicinal Chemistry, vol. 1, pp. 204–225 (1994).

Smith, C. et al., "RP 73163: A Bioavailable Alkylsulphinyl–Diphenylimidazole ACAT Inhibitor", Bioorganic & Medicinal Chemistry Letters, vol. 6, No. 1, pp. 47–50 (1996).

Sorbera, L.A. et al., "Avasimibe: Treatment of Lipoprotein Disorders, ACAT Inhibitor", Drugs of Future, vol. 24, No. 1, pp. 9–15 (1999).

Stout, D.M., "Inhibitors of Acyl–CoA:Cholesterol O–Acyl Transferase (ACAT) as Hypocholesterolemic Agents. 6. The First Water–Soluble ACAT Inhibitor with Lipid–Regulating Avtivity, etc.", Chemtracts–Organic Chemistry, vol. 8, pp. 359–362 (1995).

Takeda, K. et al., "Recessive Inheritance of Thyroid Hormone Resistance Caused by Complete Deletion of the Protein–Coding Region of the Thyroid Hormone Receptor–$\beta$ Gene", Journal of Clinical Endocrinology and Metabolism, vol. 74, No. 1, pp. 49–55 (1992).

Wermuth, C.G. et al., "Designing Prodrugs and Bioprecursors I: Carrier Prodrugs", The Practice of Medicinal Chemistry, Academic Press, Wermuth, C.G., ed., pp. 671–696 (1996).

* cited by examiner

PHENYL NAPHTHOL LIGANDS FOR THYROID HORMONE RECEPTOR

This application claims priority from U.S. Provisional Application 60/337,760 filed Dec. 7, 2001 which is incorporated herein by reference.

FIELD OF THE INVENTION

The present invention relates to novel phenyl naphthol compounds which are thyroid receptor ligands and are preferably selective for the thyroid hormone receptor β. Further, the present invention relates to methods for using such compounds and to pharmaceutical compositions containing such compounds.

BACKGROUND OF THE INVENTION

While the extensive role of thyroid hormones in regulating metabolism in humans is well recognized, the discovery and development of new specific drugs for improving the treatment of hyperthyroidism and hypothyroidism has been slow. This has also limited the development of thyroid agonists and antagonists for treatment of other important clinical indications, such as hypercholesterolemia, obesity and cardiac arrhythmias.

Thyroid hormones affect the metabolism of virtually every cell of the body. At normal levels, these hormones maintain body weight, metabolic rate, body temperature and mood, and influence blood levels of serum low density lipoprotein (LDL). Thus, in hypothyroidism there is weight gain, high levels of LDL cholesterol, and depression. In hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3',5'-tetraiodo-L-thyronine, or $T_4$) and triiodothyronine (3,5,3'-triiodo-L-thyronine, or $T_3$). However, replacement therapy, particularly in older individuals, may be restricted by certain detrimental effects from thyroid hormones.

In addition, some effects of thyroid hormones may be therapeutically useful in non-thyroid disorders if adverse effects can be minimized or eliminated. These potentially useful influences include weight reduction, lowering of serum LDL levels, amelioration of depression and stimulation of bone formation. Prior attempts to utilize thyroid hormones pharmacologically to treat these disorders have been limited by manifestations of hyperthyroidism, and in particular by cardiovascular toxicity.

Development of specific and selective thyroid hormone receptor ligands, particularly agonists of the thyroid hormone receptor could lead to specific therapies for these common disorders, while avoiding the cardiovascular and other toxicity of native thyroid hormones. Tissue-selective thyroid hormone agonists may be obtained by selective tissue uptake or extrusion, topical or local delivery, targeting to cells through other ligands attached to the agonist and targeting receptor subtypes. Thyroid hormone receptor agonists that interact selectively with the β-form of the thyroid hormone receptor offers an especially attractive method for avoiding cardio-toxicity.

Thyroid hormone receptors (TRs) are, like other nuclear receptors, single polypeptide chains. The various receptor forms appear to be products of two different genes α and β. Further isoform differences are due to the fact that differential RNA processing results in at least two isoforms from each gene. The $TR\alpha_1$, $TR\beta_1$ and $TR\beta_2$ isoforms bind thyroid hormone and act as ligand-regulated transcription factors. In adults, the $TR\beta_1$ isoform is the most prevalent form in most tissues, especially in the liver and muscle. The $TR\alpha_2$ isoform is prevalent in the pituitary and other parts of the central nervous system, does not bind thyroid hormones, and acts in many contexts as a transcriptional repressor. The $TR\alpha_1$ isoform is also widely distributed, although its levels are generally lower than those of the $TR\beta_1$ isoform. Whereas many mutations in the TRβ gene have been found and lead to the syndrome of generalized resistance to thyroid hormone, mutations leading to impaired TRα function have not been found.

A growing body of data suggests that many or most effects of thyroid hormones on the heart, and in particular, on the heart rate and rhythm, are mediated through the α-form of the $TR\alpha_1$ isoform, whereas most actions of the hormone such as on the liver, muscle and other tissues, are mediated more through the β-forms of the receptor. Thus, a TRβ-selective agonist might not elicit the cardiac rhythm and rate influences of the hormones, but would elicit many other actions of the hormones. Applicants believe that the α-form of the receptor is primarily associated with heart rate function for the following reasons:

1) tachycardia is very common in the syndrome of generalized resistance to thyroid hormone in which there are defective TRβ-forms, and high circulating levels of $T_4$ and $T_3$;

2) there was a tachycardia in the only described patient with a double deletion of the TRβ gene (Takeda et al, J. Clin. Endrocrinol. & Metab. 1992, Vol. 74, p. 49);

3) a double knockout TRα gene (but not β-gene) in mice resulted in a slower mouse heart rate, as compared to control mice; and 4) western blot analysis of human myocardial TRs show presence of the $TR\alpha_1$, $TR\alpha_2$ and $TR\beta_2$ proteins, but not $TR\beta_1$.

If these indications are correct, then it may be possible that a TRβ-selective agonist could be used to mimic a number of thyroid hormone actions, while having a lesser effect on the heart. Such a compound may be used for: (1) replacement therapy in elderly subjects with hypothyroidism who are at risk for cardiovascular complications; (2) replacement therapy in elderly subjects with subclinical hypothyroidism who are at risk for cardiovascular complications; (3) obesity; (4) hypercholesterolemia due to elevations of plasma LDL levels; (5) depression; and, (6) osteoporosis in combination with a bone resorption inhibitor.

SUMMARY OF THE INVENTION

In accordance with the illustrative embodiments and demonstrating features of the present invention, compounds are provided which are thyroid receptor ligands, and have the general formula I:

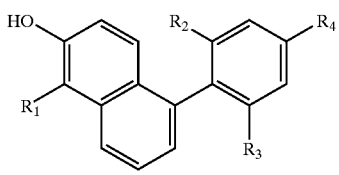

wherein;

R$_1$ is halogen, trifluoromethyl, substituted or unsubstituted aryl, substituted or unsubstituted C$_{1-6}$ alkyl, or substituted or unsubstituted C$_{3-7}$ cycloalkyl;

R$_2$ and R$_3$ are each independently hydrogen, halogen, substituted or unsubstituted C$_{1-4}$ alkyl, or substituted or unsubstituted C$_{3-6}$ cycloalkyl, wherein at least one of R$_2$ and R$_3$ is other than hydrogen;

R$_4$ is a carboxylic acid, or an ester thereof, selected from the group consisting of (CH$_2$)$_n$COOH, (CH)$_2$COOH, NHCO(CH$_2$)$_n$COOH, CONH(CH$_2$)$_n$COOH and NH(CH$_2$)$_m$COOH;

n is an integer from 0 to 4; and m is an integer from 1 to 4, including all prodrug-esters, stereoisomers and pharmaceutically acceptable salts of formula I.

The compounds of formula I are thyroid hormone receptor ligands, and include compounds which are, for example, selective agonists, partial agonists, antagonists or partial antagonists of the thyroid receptor. Preferably the compounds of formula I possess activity as agonists of the thyroid receptor, preferably selective agonists of the thyroid receptor-beta, and may be used in the treatment of diseases or disorders associated with thyroid receptor activity. In particular, the compounds of formula I may be used in the treatment of diseases or disorders associated with metabolism dysfunction or which are dependent upon the expression of a T$_3$ regulated gene, such as obesity, hypercholesterolemia, atherosclerosis, cardiac arrhythmias, depression, osteoporosis, hypothyroidism, goiter, thyroid cancer, glaucoma, skin disorders or diseases and congestive heart failure.

The present invention provides for compounds of formula I, pharmaceutical compositions employing such compounds and for methods of using such compounds. In particular, the present invention provides for a pharmaceutical composition comprising a therapeutically effective amount of a compound of formula I, alone or in combination with a pharmaceutically acceptable carrier.

Further, in accordance with the present invention, a method is provided for preventing, inhibiting or treating the progression or onset of diseases or disorders associated with the thyroid receptor, particularly, the thyroid receptor-beta, such as the diseases or disorders defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of formula I and another type of therapeutic agent, is administered to a mammalian species in need of treatment.

Preferably, compounds of this invention include embodiments of formula I wherein:

R$_1$ is selected from the group consisting of halogen, substituted or unsubstituted C$_{1-3}$ alkyl and substituted or unsubstituted aryl;

R$_2$ and R$_3$ are each independently hydrogen or chloro, wherein at least one of R$_2$ and R$_3$ is chloro;

R$_4$ is selected from the group consisting of NHCO(CH$_2$)$_n$COOH, NH(CH$_2$)$_m$COOH, CONHCH$_2$COOH and CH$_2$COOH;

n is an integer from 0 to 1; and m is an integer from 1 to 2.

Particularly preferred embodiments include compounds of formula I wherein:

R$_1$ is bromo or substituted or unsubstituted C$_{1-3}$ alkyl;

R$_2$ and R$_3$ are chloro;

R$_4$ is NHCO(CH$_2$)$_n$COOH or NH(CH$_2$)$_m$COOH;

n is an integer from 0 to 1; and m is an integer from 1 to 2.

Specific examples of the preferred compounds of the invention have the structures:

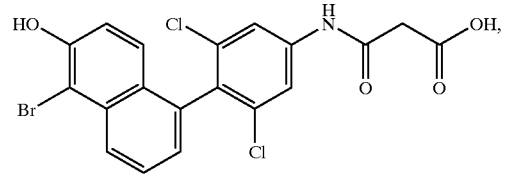

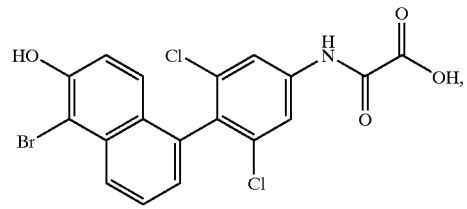

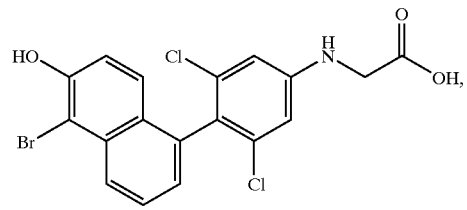

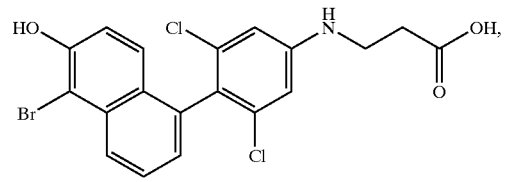

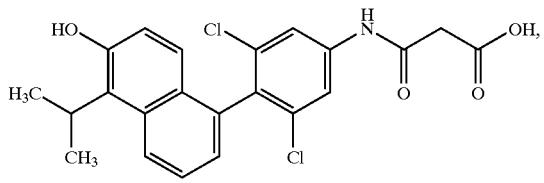

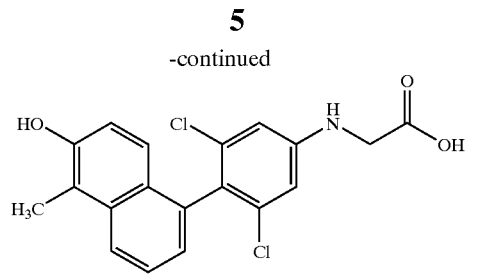

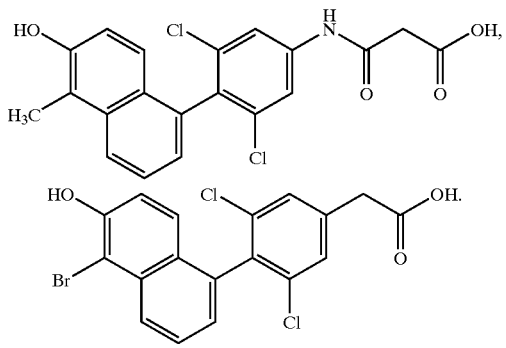

or an alkyl ester thereof.

Particularly preferred are compounds of the invention having the structures:

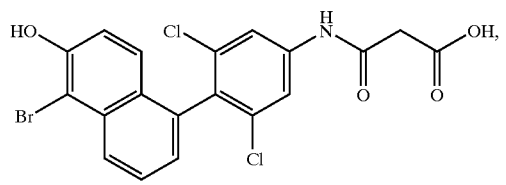

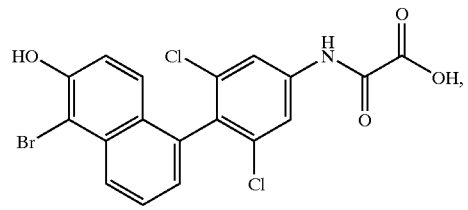

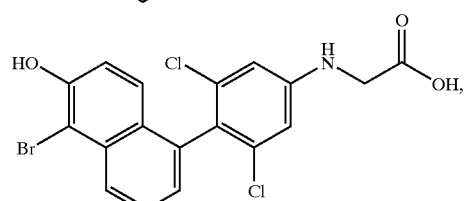

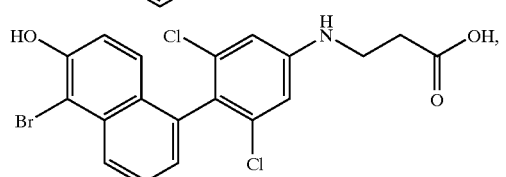

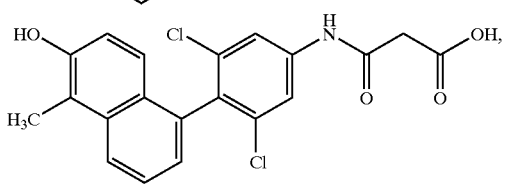

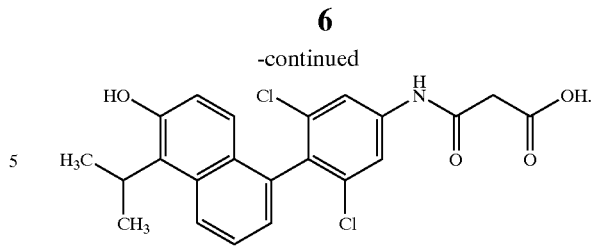

or alkyl esters thereof, such as the methyl or ethyl ester.

DETAILED DESCRIPTION OF THE INVENTION

The following definitions apply to the terms as used throughout this specification, unless otherwise limited in specific instances.

The term "thyroid receptor ligand" as used herein is intended to cover any moiety which binds to a thyroid receptor. The ligand may act as an agonist, an antagonist, a partial agonist or a partial antagonist. Another term for "thyroid receptor ligand" is "thyromimetic".

Unless otherwise indicated, the term "alkyl" as employed herein alone or as part of another group includes both straight and branched chain hydrocarbons, containing 1 to 12 carbons in the normal chain, preferably 1 to 6 carbons, such as methyl, ethyl, propyl, isopropyl, butyl, t-butyl, or isobutyl, pentyl, hexyl, isohexyl, heptyl, 4,4-dimethylpentyl, octyl, 2,2,4-trimethylpentyl, nonyl, decyl, undecyl, dodecyl. "Substituted alkyl" includes an alkyl group optionally substituted with one or more functional groups which are commonly attached to such chains, such as, alkyl, alkenyl, alkynyl, aryl, cycloalkyl, heteroaryl, hydroxy, cyano, nitro, amino, halogen, carboxyl or alkyl ester thereof and/or carboxamide, substituted or unsubstituted.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl). "Substituted aryl" includes an aryl group optionally substituted through available carbon atoms with one or more groups selected from hydrogen, halogen, alkyl, haloalkyl, alkoxy, haloalkoxy, alkenyl, trifluoromethyl, trifluoromethoxy, alkynyl, hydroxy, amino, nitro, cyano and/or any of the alkyl substituents set out herein.

The term "halogen" as used herein alone or as part of another group refers to chlorine, bromine, iodine and fluorine, with chlorine or bromine being preferred.

The term "cycloalkyl" as used herein includes saturated or partially saturated (containing one or more double bonds) cyclic hydrocarbon groups containing 3 to 7 carbon atoms, such as cyclopropyl, cyclobutyl, cyclopentyl, cyclohexyl. "Substituted cycloalkyl" includes a cycloalkyl group optionally substituted with one or more substituents, such as those described for alkyl and/or aryl.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms that may be unsubstituted or substituted, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methanesulfonic acid or p-toluenesulfonic acid. Corresponding acid addition salts can also be formed having, if desired, an additionally present basic center. If the compounds of formula I have at least one acid group, (i.e., COOH) they can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tertbutyl, diethyl, diisopropyl, triethyl, tributyl or dimethylpropylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I, or their pharmaceutically acceptable salts, are also included.

Preferred salts of the compounds of formula I, which contain a basic group, include monohydrochloride, hydrogensulfate, methanesulfonate, phosphate or nitrate.

Salts of the compounds of formula I, which contain an acid group, preferably include sodium, potassium and magnesium salts and pharmaceutically acceptable organic amines.

The compounds of formula I may also have prodrug forms. Any compound that will be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are in:
a.) *The Practice of Medicinal Chemistry*, Camille G. Wermuth et al., Ch 31, (Academic Press, 1996);
b.) *Design of Prodrugs*, edited by H. Bundgaard, (Elsevier, 1985); and
c.) *A Textbook of Drug Design and Development*, P. Krogsgaard-Larson and H. Bundgaard, eds. Ch 5, pg. 113–191 (Harwood Academic Publishers, 1991).
Said references are incorporated herein by reference.

Embodiments of prodrugs suitable for use in the present invention include alkyl esters, such as ethyl ester, or acyloxyalkyl esters, such as pivaloyloxymethyl (POM).

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant invention are contemplated, either in admixture or in pure or substantially pure form. The compounds of the present invention can have asymmetric centers at any of the carbon atoms, including any one of the R substituents. Consequently, compounds of formula I can exist in astereometric forms or in mixtures thereof. The below described processes can utilize racemates, enantiomers or diasteromers as starting materials. When diastereomeric products are prepared, they can be separated by any known conventional method. For example, they can be separated by chromatographic or fractional crystallization.

The compounds of formula I of the invention can be prepared as shown in the following reaction schemes and description thereof, as well as by relevant published literature procedures that may be used by one skilled in the art. Exemplary reagents and procedures for these reactions appear hereinafter and in the working Examples. Protection and deprotection in the Schemes below may be carried out by procedures generally known in the art. For example, see T. W. Greene & P. G. M. Wuts, "Protecting Groups in Organic Synthesis", 3$^{rd}$ Edition, (Wiley, 1999), incorporated herein by reference.

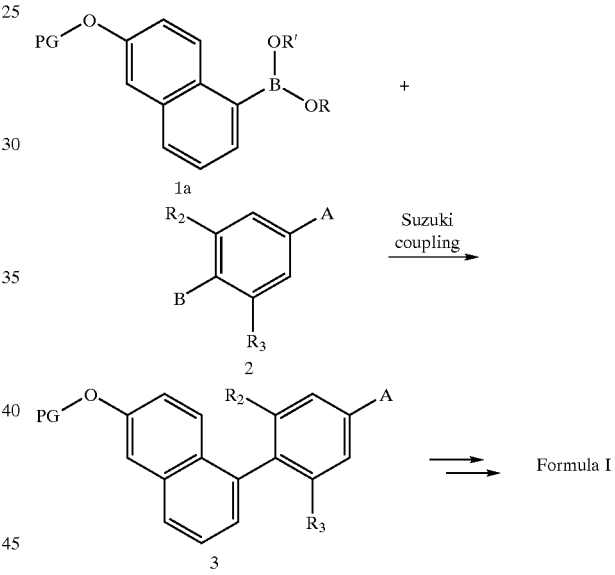

SCHEME 1

Scheme 1 depicts a general reaction sequence used in the synthesis of Examples 1–16 to produce the compounds of formula I. Boronic acid, indicated by the compound of formula 1a (R=R'=H) or its pinacol ester (R=RI=C(CH$_3$)$_2$ C(CH$_3$)$_2$) can be reacted with a compound of formula 2 using conditions commonly employed for a Suzuki reaction (T. R. Hoye, M. Chen, J. Org. Chem., 61, 7940–7942, 1996; T. R. Hoye, L. Mi, Tetrahedron Lett., 37, 3097–3098, 1996; U. Anton, C. Goeltner, K. Muellen, Chem. Ber., 125, 2325–2330, 1992; U. Anton, M. Adam, M. Wagner, Q.-L. Zhou, K. Muellen, Chem. Ber., 126, 517–521, 1993; W.-C. Shieh, J. A. Carlson, J. Org. Chem., 57, 379–381, 1992; Y. Nakano, D. Imai, Synthesis, 12, 1425–1428, 1997; S. Kumar, J. Org. Chem., 62, 8535–8539, 1997; C. G. Blettner et al., J. Org. Chem., 64, 3885–3890, 1999). The B group in formulas 2 and 3 represent a functional group commonly present in reagents used in combination with boronic acids or their esters for the formation of a carbon-carbon bond, namely I, Br, or OSO$_2$CF$_3$. The A group in formulas 2 and 3 represents, in separate examples, nitro ($NO_2$), the ester of a carboxylic acid (COOR, R=Me or Et), the ester of acetic acid ($CH_2COOR$, R=Me or Et) or other groups compatible with the reaction conditions. A suitable A group is chosen to allow further chemical modification and elaboration to provide the $R_4$ groups defined for the compounds of formula I. For example, when A is nitro, the nitro group can be reduced to an amino group and subsequently acylated or alkylated. Further, installation of lipophilic groups at $R_1$ for the compound of formula I was accomplished by electrophilic substitution using, for example, elemental bromine or acetic anhydride. However, synthesis of the compounds of formula I is not limited by the examples, such that chemical modification of group A or B, or installation of any of the R groups of formula I, may be accomplished by any other suitable means known to those skilled in the art.

6-methoxy-tetralone; see T. Kasturi, T. Arunachalam, Can. J. Chem., 46, 3625–3629, 1968) and 2,6-dichloro-4-nitrophenol 7. Thus, naphthol 4 is reacted with trifluoromethyl sulfonic acid anhydride in dichloromethane at −40° C. to provide the compound of formula 5. The pinacol boronate ester of formula 6 is formed by the reaction of the compound of formula 5 with bis(pinacolato)diborane in the presence of a 1,1'-[bis(diphenylphosphino)ferrocene]-dichloropalladium(II) and potassium acetate using established procedures, such as those described in T. Ishiyama, M. Murata, N. Miyaura, J. Org. Chem., 60, 7508–7510, 1995; M. Murata, S. Watanabe, Y. Masuda, J. Org. Chem., 62, 6458–6459, 1997; J. Frahn, A.-D. Schleuter, Synthesis, 11, 1301–1304, 1997; S. R. Piettre, S. Baltzer, Tetrahedron Lett., 38, 1197–1200, 1997. Triflate of formula 8 is independently prepared by the reaction of phenol 7 with trifluo-

SCHEME 2

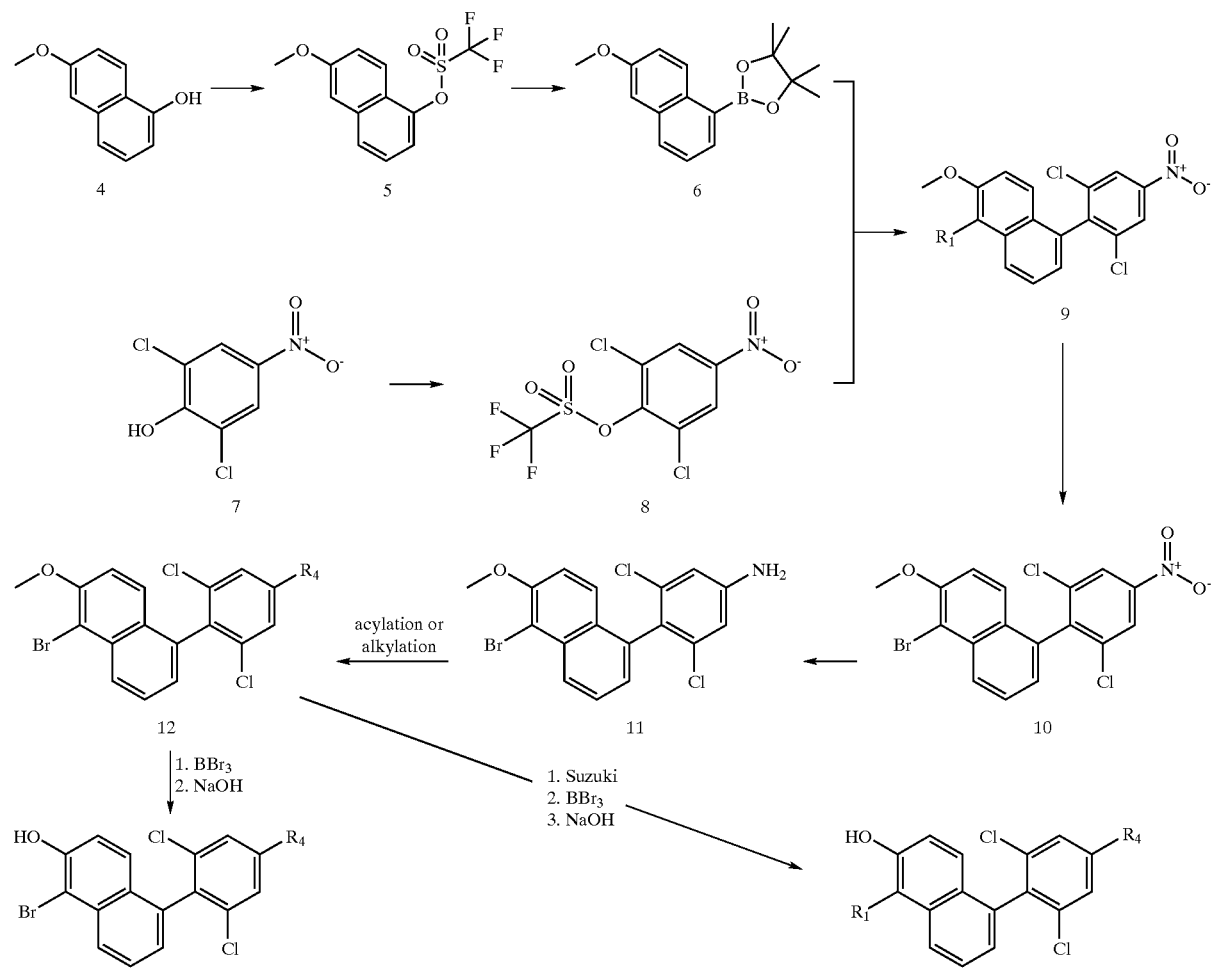

Scheme 2 is a detailed reaction scheme utilized for the synthesis of Examples 1–5 and 7–9 hereinafter. Synthesis of the core phenyl naphthyl system was carried out in four steps from naphthol of formula 4 (naphthol 4 is a known compound and is synthesized from commercially available romethyl sulfonic acid anhydride in dichloro-methane at −40° C. Intermediate 9 was prepared by carbon-carbon bond formation between intermediate 6 and 8, carried out under conditions commonly employed for a Suzuki reaction; specifically, in dimethoxy-ethane:water (3:1) with sodium carbonate as base and tetrakis(triphenylphosphine)
palladium(0) as catalyst. Installation of bromine at RI was
accomplished by reacting intermediate 9 with elemental
bromine in dichloromethane to yield intermediate 10. The
nitro group of intermediate 10 was reduced using iron(0) in
aqueous acetic acid. For Example 1, the amino group of
intermediate 11 was acylated with ethyl 3-chloro-3-
oxopropanoate in the presence of triethylamine in dichlo-
romethane to form $R_4$ as indicated. The intermediate ester
was treated first with boron tribromide in dichloromethane at
0° C. to demethylate the naphthol followed by hydrolysis of
the ester with aqueous sodium hydroxide in methanol. This
general three step procedure, acylation or alkylation fol-
lowed by removal of the methyl group with boron tribro-
mide and hydrolysis of the ester at $R_4$, was applied during
the synthesis of Examples 2–5 hereinafter.

Examples 7–9 hereinafter were synthesized by further
modification at $R_1$ by reacting intermediate bromide 12
separately with phenyl boronic acid in the presence of
sodium carbonate and tetrakis(triphenylphosphine)-
palladium(0) or methyl boronic acid (T. Harada et al.,
Synlett, 3, 283–284, 1995) in the presence of tribasic potas-
sium phosphate and 1,1'-[bis(diphenyl-phosphino)-
ferrocene]dichloropalladium(II). The intermediates so
obtained were subjected to boron tribromide and sodium
hydroxide as described for Example 1 hereinafter.

By suitable application of the procedures described
above, Examples 10–15 hereinafter may be constructed. In
these examples, the ester of a carboxylic acid is further
modified by hydrolysis of the ester with, for example,
aqueous sodium hydroxide in methanol, or by hydrolysis
followed by amide coupling using, for example, 1-[3-
(dimethylamino)propyl]-3-ethylcarbodiimide
hydrochloride, 1-hydroxy-7-azabenzotriazole and a base
such as triethylamine in a suitable solvent. These chemical
transformations are well established in the literature.

Utilities & Combinations
A. Utilities

The compounds of the present invention are thyroid
receptor ligands, and include compounds which are, for
example, selective agonists, partial agonists, antagonists or
partial antagonists of the thyroid receptor. Preferably com-
pounds of the present invention possess activity as agonists
of the thyroid receptor, preferably selective agonists of the
thyroid receptor-beta, and may be used in the treatment of
diseases or disorders associated with thyroid receptor activ-
ity. In particular, compounds of the present invention may be
used in the treatment of diseases or disorders associated with
metabolism dysfunction or which are dependent upon the
expression of a $T_3$ regulated gene.

Accordingly, the compounds of the present invention can
be administered to mammals, preferably humans, for the

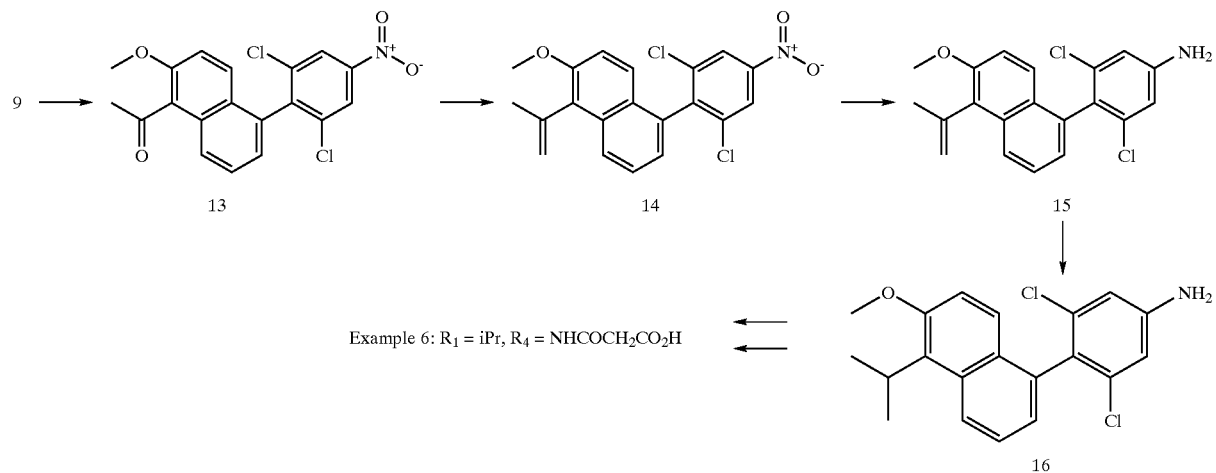

SCHEME 3

Example 6: $R_1$ = iPr, $R_4$ = NHCOCH$_2$CO$_2$H

Scheme 3 shows the route taken for the synthsis of
Example 5 hereinafter. Installation of the iso-propyl group at
$R_1$ of intermediate 9 from Scheme 2 was carried out in three
steps. Intermediate 9 was reacted with acetic anhydride in
the presence of boron trifluoride dimethylsulfide complex in
dichloromethane. Intermediate 13 was reacted with Nysted
reagent (L. Nysted, U.S. Pat. No. 3,865,848; S. Matsubara,
M. Sugihara, K. Utimoto, Synlett, 3, 131–315, 1998; G. S.
Bisacchi, J. E. Sundeen, PCT Int. App. WO 9809964 A1
19980312) in the presence of titanium tetrachloride in
dichloromethane to yield an olefin 14. Reduction of the nitro
group was carried out as described in the explanation of
Scheme 2, to give aniline 15. Reduction of the double bond
of compound 15 was carried out under an atmosphere of
hydrogen using platinum oxide as a catalyst to give inter-
mediate 16. Intermediate 16 was further modified at $R_4$
using the procedures described in Scheme 2 for Example
1–5 and 7–9.

treatment of a variety of conditions and disorders, including,
but not limited to hypothyroidism; subclinical hyperthyroid-
ism; non-toxic goiter; atherosclerosis; thyroid hormone
replacement therapy (e.g., in the elderly); malignant tumor
cells containing the thyroid receptor; papillary or follicular
cancer; maintenance of muscle strength and function (e.g., in
the elderly); reversal or prevention of frailty or age-related
functional decline ("ARFD") in the elderly (e.g.,
sarcopenia); treatment of catabolic side effects of glucocor-
ticoids; prevention and/or treatment of reduced bone mass,
density or growth (e.g., osteoporosis and osteopenia); treat-
ment of chronic fatigue syndrome (CFS); accelerating heal-
ing of complicated fractures, e.g. distraction osteogenesis; in
joint replacement; eating disorders (e.g., anorexia); treat-
ment of obesity and growth retardation associated with
obesity; treatment of depression, nervousness, irritability
and stress; treatment of reduced mental energy and low
self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of hyperinsulinemia; stimulation of osteoblasts, bone remodeling and cartilage growth; regulation of food intake; treatment of insulin resistance, including NIDDM, in mammals (e.g., humans); treatment of insulin resistance in the heart; treatment of congestive heart failure; treatment of musculoskeletal impairment (e.g., in the elderly); improvement of the overall pulmonary function; skin disorders or diseases, such as glucocorticoid induced dermal atrophy, including restoration of dermal atrophy induced by topical glucocorticoids, and the prevention of dermal atrophy induced by topical glucocorticoids (such as the simultaneous treatment with topical glucocorticoid or a pharmacological product including both glucocorticoid and a compound of the invention), the restoration/prevention of dermal atrophy induced by systemic treatment with glucocorticoids, restoration/prevention of atrophy in the respiratory system induced by local treatment with glucocorticoids, UV-induced dermal atrophy, dermal atrophy induced by aging (wrinkles, etc.), wound healing, keloids, stria, cellulite, roughened skin, actinic skin damage, lichen planus, ichtyosis, acne, psoriasis, Dernier's disease, eczema, atopic dermatitis, chloracne, pityriasis and skin scarring.

The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727–34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may employed in combination with other modulators and/or ligands of the thyroid receptor or other suitable therapeutic agents useful in the treatment of the aforementioned disorders including: anti-diabetic agents; anti-osteoporosis agents; anti-obesity agents; growth promoting agents (including growth hormone secretagogues); anti-inflammatory agents; anti-anxiety agents; anti-depressants; anti-hypertensive agents; cardiac glycosides; cholesterol/lipid lowering agents; appetite suppressants; bone resorption inhibitors; thyroid mimetics (including other thyroid receptor agonists); anabolic agents; and anti-tumor agents.

Examples of suitable anti-diabetic agents for use in combination with the compounds of the present invention include biguanides (e.g., metformin or phenformin), glucosidase inhibitors (e.g,. acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2), glucagon-like peptide-1 (GLP-1), and dipeptidyl peptidase IV (DP4) inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-obesity agents for use in combination with the compounds of the present invention include aP2 inhibitors, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), other thyroid receptor beta drugs, such as a thyroid receptor ligand as disclosed in WO 97/21993 (U. Cal SF), WO 99/00353 (KaroBio) and GB98/284425 (KaroBio), and/or an anorectic agent, such as dexamphetamine, phentermine, phenylpropanolamine or mazindol.

The compounds of the present invention may be combined with growth promoting agents, such as, but not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention may also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-HT$_D$ agonists, such as sumatriptan, or agents which inhibit somatostatin or its release, such as physostigmine and pyridostigmine. A still further use of the disclosed compounds of the invention is in combination with parathyroid hormone, PTH(1–34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et al., *Bio. Med. Chem. Let.*, 9, 1003–1008 (1999) and Hamann, L. G. et al., *J. Med. Chem.*, 42, 210–212 (1999).

A further use of the compounds of this invention is in combination with steriodal or non-steroidal progesterone receptor agonists ("PRA"), such as levonorgestrel, medroxyprogesterone acetate (MPA).

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists,(e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

For the treatment of skin disorders or diseases as described above, the compounds of the present invention may be used alone or optionally in combination with a retinoid, such as tretinoin, or a vitamin D analog.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors, squalene synthetase inhibitors, fibrates, bile acid sequestrants, ACAT inhibitors, MTP inhibitors, lipooxygenase inhibitors, an iheal Na+/bile acid cotransporter inhibitor, cholesterol absorption inhibitors, and cholesterol ester transfer protein inhibitors (e.g., CP-529414).

MTP inhibitors which may be employed herein in combination with one or more compounds of formula I include MTP inhibitors as disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440 all incorporated herein by reference.

A preferred MTP inhibitor is

9-[4-[4-[[2-(2,2,2-Trifluoroethoxy)benzoyl]amino]-1-piperidinyl]butyl]-N-(2,2,2-trifluoroethyl)-9H-fluorene-9-carboxamide

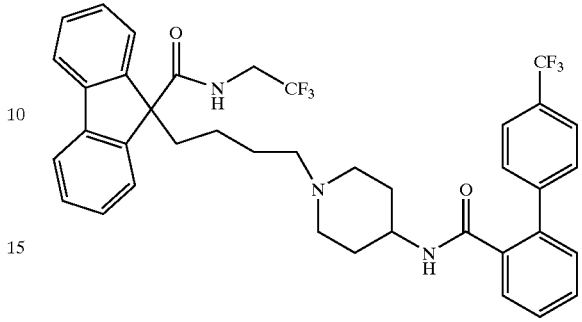

The HMG CoA reductase inhibitors which may be employed in combination with one or more compounds of formula I include mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Further HMG CoA reductase inhibitors which may be employed herein include fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No.0,142,146 A2, as well as other known HMG CoA reductase inhibitors.

The squalene synthetase inhibitors which may be used in combination with the compounds of the present invention include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinylmethyl) phosphonates, terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, as well as other squalene synthetase inhibitors as disclosed in U.S. Pat. No. 4,871,721 and 4,924,024 and in Biller, S. A., Neuenschwander, K., Ponpipom, M. M., and Poulter, C. D., Current Pharmaceutical Design, 2, 1–40 (1996).

Bile acid sequestrants which may be used in combination with the compounds of the present invention include cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

ACAT inhibitors suitable for use in combination with compounds of the invention include ACAT inhibitors as described in, Drugs of the Future 24, 9–15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62.

Examples of suitable cholesterol absorption inhibitor for use in combination with the compounds of the invention include SCH48461 (Schering-Plough), as well as those disclosed in Atherosclerosis 115, 45–63 (1995) and J. Med. Chem. 41, 973 (1998).

Examples of suitable ileal $Na^+$/bile acid cotransporter inhibitors for use in combination with the compounds of the invention include compounds as disclosed in Drugs of the Future, 24, 425–430 (1999).

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

The aforementioned patents and patent applications are incorporated herein by reference.

The above other therapeutic agents, when employed in combination with the compounds of the present invention, may be used, for example, in those amounts indicated in the Physicians' Desk Reference (PDR) or as otherwise determined by one of ordinary skill in the art.

Where the compounds of the invention are utilized in combination with one or more other therapeutic agent(s), either concurrently or sequentially, the following combination ratios and dosage ranges are preferred:

When combined with a hypolypidemic agent, an antidepressant, a bone resorption inhibitor and/or an appetite suppressant, the compounds of formula I may be employed in a weight ratio to the additional agent within the range from about 500:1 to about 0.005:1, preferably from about 300:1 to about 0.01:1.

Where the antidiabetic agent is a biguanide, the compounds of formula I may be employed in a weight ratio to biguanide within the range from about 0.01:1 to about 100:1, preferably from about 0.5:1 to about 2:1.

The compounds of formula I may be employed in a weight ratio to a glucosidase inhibitor within the range from about 0.01:1 to about 100:1, preferably from about 0.5:1 to about 50:1.

The compounds of formula I may be employed in a weight ratio to a sulfonylurea in the range from about 0.01:1 to about 100:1, preferably from about 0.2:1 to about 10:1.

The compounds of formula I may be employed in a weight ratio to a thiazolidinedione in an amount within the range from about 0.01:1 to about 100:1, preferably from about 0.5:1 to about 5:1.

The thiazolidinedione may be employed in amounts within the range from about 0.01 to about 2000 mg/day, which may optionally be administered in single or divided doses of one to four times per day.

Further, where the sulfonylurea and thiazolidinedione are to be administered orally in an amount of less than about 150 mg, these additional agents may be incorporated into a combined single tablet with a therapeutically effective amount of the compounds of formula I.

Metformin, or salt thereof, may be employed with the compounds of formula I in amounts within the range from about 500 to about 2000 mg per day, which may be administered in single or divided doses one to four times daily.

The compounds of formula I may be employed in a weight ratio to a PPAR-alpha agonist, a PPAR-gamma agonist, a PPAR-alpha/gamma dual agonist, an SGLT2 inhibitor and/or an aP2 inhibitor within the range from about 0.01:1 to about 100:1, preferably from about 0.5:1 to about 5:1.

An MTP inhibitor may be administered orally with the compounds of formula I in an amount within the range of from about 0.01 mg/kg to about 100 mg/kg and preferably from about 0.1 mg/kg to about 75 mg/kg, one to four times daily.

A preferred oral dosage form, such as tablets or capsules, may contain the MTP inhibitor in an amount of from about 1 to about 500 mg, preferably from about 2 to about 400 mg, and more preferably from about 5 to about 250 mg, administered on a regimen of one to four times daily.

For parenteral administration, the MTP inhibitor may be employed in an amount within the range of from about 0.005 mg/kg to about 10 mg/kg and preferably from about 0.005 mg/kg to about 8 mg/kg, administered on a regimen of one to four times daily.

A HMG CoA reductase inhibitor may be administered orally with the compounds of formula I within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A squalene synthetase inhibitor may be administered with the compounds of formula I within the range of from about 10 mg to about 2000 mg and preferably from about 25 mg to about 200 mg.

A preferred oral dosage form, such as tablets or capsules, will contain the squalene synthetase inhibitor in an amount of from about 10 to about 500 mg, preferably from about 25 to about 200 mg.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

The following working Examples serve to better illustrate, but not limit, some of the preferred embodiments of the present invention.

EXAMPLE 1

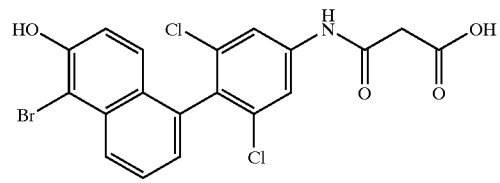

3-[3,5-dichloro-4-(5-bromo-6-hydroxynaphthyl)-phenyl]-3-amino-3-oxopropanoic acid Compound 1a:

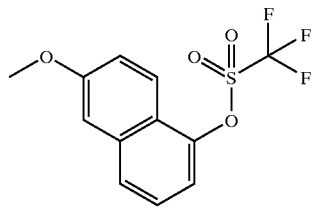

6-Methoxynaphth-1-ol (0.5 g, 2.8 mmol) and triethylamine (313 mg, 3.1 mmol) were dissolved in anhyd dichloromethane (28 mL) under a blanket of argon and cooled to −40° C. Triflic anhydride (891 mg, 3.1 mmol) was added dropwise. The reaction was warmed to −10° C. and stirred for an additional 1.5 h. Additional triflic anhydride (291 mg, 0.3 mmol) was added to complete the reaction. The reaction was quenched with water. The layers were separated and the organic layer washed with water and brine, dried over magnesium sulfate, filtered and dried in vacuo to yield 877 mg (99%) of an oil which solidifies upon standing. 1H-NMR is consistent with the proposed structure.

Compound 1b:

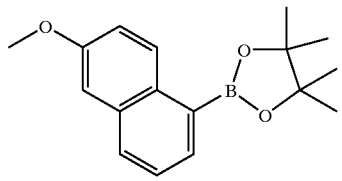

The triflate of Compound 1a (857 mg, 2.8 mmol), bis-picolinatodi-borane (1.07 g, 4.2 mmol) and anhyd potassium acetate (824 mg, 8.4 mmol) were placed in a one necked flask equipped with an argon inlet. The solids were suspended in anhyd DMSO (16 mL) and degassed by nitrogen sparge for 10 min. PdCl$_2$dppf dichloromethane (457 mg, 0.56 mmol) was added. The reaction mixture was heated to 80° C. for 4 hrs. After cooling to room temperature, the reaction was diluted with ethyl acetate and washed with half saturated brine (3×), followed by brine (1×), than dried over anhyd magnesium sulfate, filtered and evaporated in vacuo. The title compound (461 mg, 58%) was obtained by flash chromatography (115 g silica gel, isocratic elution with 5% ethyl acetate in hexanes). 1H-NMR and 13C-NMR are consistent with the proposed structure.

Compound 1c:

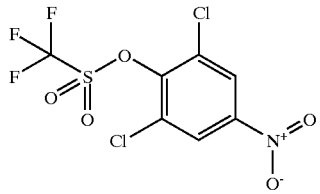

2,6-Dichloro-4-nitrophenol (626 mg, 3.0 mmol) and triethyl amine (334 mg, 460 μL, 3.3 mmol) were dissolved in anhyd dichloromethane (30 mL). The solution was cooled to −40° C. Triflic anhydride (928 mg, 553 μL, 3.3 mmol) was added dropwise and the reaction was warmed to −10° C. for 1.5 h. The reaction was quenched with water and the layers separated. The organic layer was washed with water and brine, dried over anhyd magnesium sulfate, filtered and evaporated in vacuo to yield a light tan solid (1.0 g, 99%). 1H-NMR was consistent with the proposed structure.

Compound 1d:

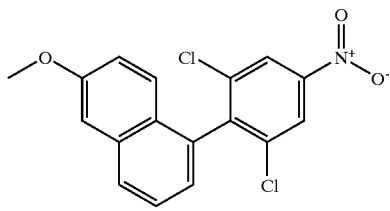

1,1,2,2,-tetramethylethyl 6-methoxynaphth-1-boronate ester (300 mg, 1.01 mmol) and the triflate of 2,6-dichloro-4-nitrophenol (721 mg, 2.12 mmol) were dissolved in 1,2-dimethoxyethane (30 mL) and degassed by nitrogen sparge for 10 min. Palladium tetrakis(triphenyl-phosphine) (231 mg, 0.2 mmol) and an aqueous solution of sodium carbonate (337 mg, 3.18 mmol) in 9 mL of water were added to the flask and the reaction mixture was heated to 80° C. for 30 min. The reaction was cooled to room temperature and diluted with ethyl acetate, washed with water and brine, dried over anhyd magnesium sulfate, filtered and evaporated in vacuo. The product was isolated by flash chromatography (62 g silica gel; isocratic elution with 10% ethyl acetate in hexanes) to yield 254 mg (69%). 1H-NMR was consistent with the proposed structure.

Compound 1e:

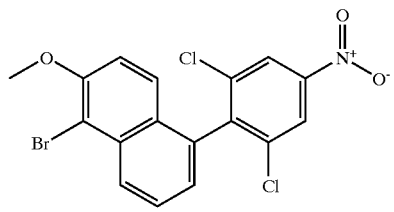

1-(2',6'-dichloro-4'-nitrophenyl)-6-methoxynaphthylene (194 mg, 0.56 mmol) was dissolved in dichloromethane (4 mL) and treated with bromine (98 mg, 0.61 mmol). The reaction was complete in 15 min. The reaction was washed with 5% aqueous sodium bisulfite, saturated aqueous sodium bicarbonate and brine, dried over magnesium sulfate, filtered and dried in vacuo to yield 212 mg (88%). 1H-NMR was consistent with the proposed structure.

Compound 1f:

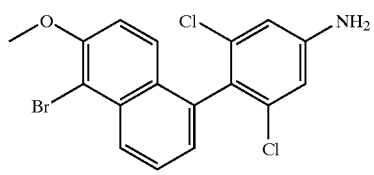

5-bromo-1-(2',6'-dichloro-4'-nitrophenyl)-6-methoxy-naphthylene (200 mg, 0.65 mmol) was suspended in acetic acid (40 mL) and water (4 mL) and heated gently to dissolve. Iron powder (363 mg, 6.5 mmol) was added and the reaction stirred vigorously over night. The reaction was diluted with ethyl acetate, filtered through a pad of celite, washed with water and brine, dried over magnesium sulfate, filtered and dried in vacuo to yield an off-white foam (200 mg, 99%). 1H-NMR was consistent with the proposed structure.

Compound 1g:

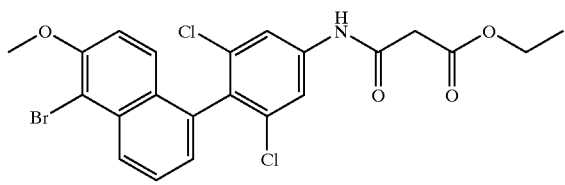

5-bromo-1-(2,6-dichloro-4-aminophenyl)-6-methoxynaphthyl-ene (200 mg, 0.65 mmol) and triethylamine (16 mg, 0.154 mmol) were dissolved in anhyd dichloromethane (1.0 mL) and cooled to 0° C. Ethyl 3-chloro-3-oxopropanoate (20 mg, 0.13 mmol) was added and the reaction was warmed to room temperature and stirred for 2 hrs. The reaction mixture was diluted with ethyl acetate, washed with water and brine, dried over magnesium sulfate, filtered and evaporated in vacuo to yield 62 mg (99%) of an off white solid. 1H-NMR was consistent with the proposed structure.

The malonic ester formed by Compound 1g (62 mg, 0.124 mmol) was dissolved in anhyd dichloromethane (1.1 mL) under a blanket of argon and cooled to −78° C. Neat boron tribromide (310 mg,1.24 mmol) was added dropwise. The reaction was warmed to 0° C. and stirred for ca. 30 min. The reaction was poured into a mixture of saturated ammonium chloride and ethyl acetate. The layers were separated and the organic extracts washed with brine, dried over anhyd magnesium sulfate, filtered and evaporated in vacuo. The crude demethylated product was dissolved in methanol and treated with 1 N sodium hydroxide (0.75 mmol) and stirred at room temperature for 1 hr. Methanol was removed in vacuo. The residue was dissolved in water and acidified to pH 1 with 1 N hydrochloric acid. The product was extracted into ethyl acetate. The combined extracts were washed with brine, dried over anhyd magnesium sulfate, filtered and evaporated in vacuo to give 38 mg (83% yield) of the title compound of Example 1. 1H-NMR and mass spec are consistent with the proposed structure.

EXAMPLE 2

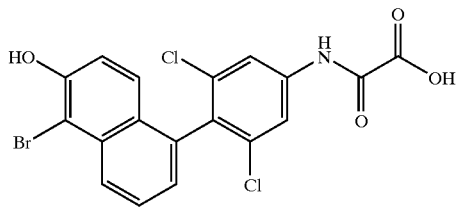

2-[3,5-dichloro-4-(5-bromo-6-hydroxynaphthyl)-phenyl]-2-amino-2-oxoacetic acid

Compound 2a:

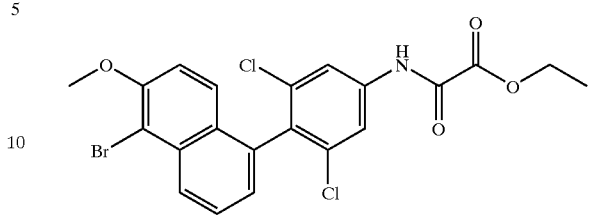

Compound 1f (397 mg, 1.0 mmol) and triethyl amine (120 mg, 1.2 mmol) were dissolved in anhyd dichloromethane (5 mL) and cooled to 0° C. Ethyl chlorooxolate (163 mg, 1.2 mmol) was added dropwise. The reaction was warmed to room temperature and stirred overnight. The reaction was diluted with ethyl acetate and washed with water and brine, dried over anhyd magnesium sulfate, filtered and dried in vacuo. Flash chromatography (30 g silica gel, elute with 15% ethyl acetate in hexanes) provided pure product (298 mg, 60%). 1H-NMR was consistent with the proposed structure.

The ester formed by Compound 2a (60 mg, 0.12 mmol) was deprotected using the protocol described for Compound 1h yielding 25 mg, (55%) of the title compound of Example 2. 1H-NMR and mass spec were consistent with the proposed structure of Example 2.

EXAMPLE 3

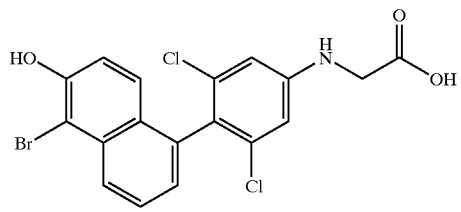

N-[3,5-dichloro-4-(5-bromo-6-hydroxynaphthyl)-phenyl]-glycine

Compound 3a:

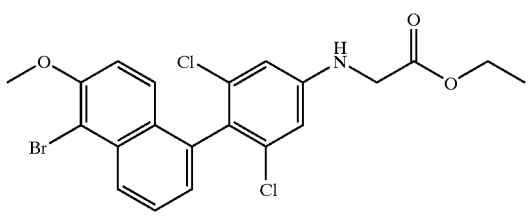

Compound 1f (50 mg, 0.126 mmol) was dissolved in anhyd acetonitrile (1 mL) and treated with potassium carbonate (19 mg, 0.139 mmol) and ethyl bromoacetate (23 mg, 0.139 mmol). The reaction was heated to 80° C. for 2 h. Very little reaction was evident. Additional ethyl bromoacetate (112 mg, 0.68 mmol) was added. Heating was continued overnight. The reaction was diluted with ethyl acetate and water. The layers were separated and the organic layer was washed with water and brine, dried over anhyd magnesium sulfate, filtered and evaporated in vacuo. The crude product was carried onto the next step without further purification.

The ester formed by Compound 3a (60 mg, 0.12 mmol) was deprotected using the protocol described for compound 1 hr yielding 45 mg (55%) of the title Compound of Example 3. 1H-NMR and mass spec were consistent with the proposed structure.

EXAMPLE 4

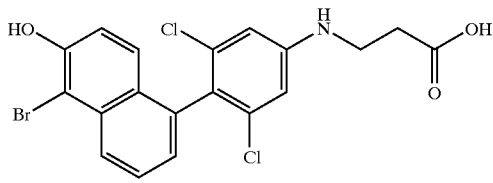

3-[3,5-dichloro-4-(5-bromo-6-hydroxynaphthyl)-phenyl]-3-aminopropanoic acid

Compound 4a:

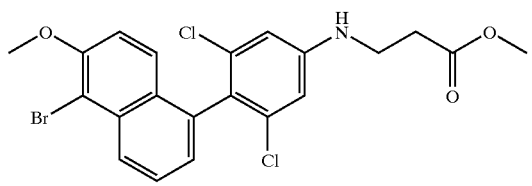

Compound 1f (45 mg, 0.113 mmol) was dissolved in acetic acid (64 μL). Methyl acrylate was added and the reaction mixture was heated to 117° C. Very little reaction had occurred in 1.5 hrs. Additional acetice acid (650 μL) and methyl acrylate (490 mg, 5.6 mmol) were added. The reaction was heated at 117° C. overnight. The reaction was cooled to room temperature, diluted with ethyl acetate, washed with water and brine, dried over anhyd magnesium sulfate, filtered and evaporated to dryness. The crude product mixture (55 mg) was carried onto the next step without further purification.

The product from Compound 4a (55 mg) was deprotected using the protocol described for Compound 1h. The title compound of Example 4 (11 mg, 21%) was isolated by silica gel chromatography (2.5 g silica gel, elute with 50% ethyl acetate in hexanes (100 mL) followed by 50% ethyl acetate in hexanes containing 1% acetic acid). 1H-NMR and mass spec were consistent with the proposed structure.

EXAMPLE 5

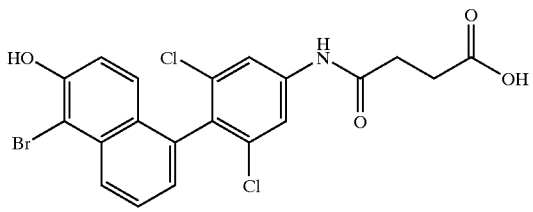

4-[3,5-dichloro-4-(5-bromo-6-hydroxynaphthyl)-phenyl]-4-amino-4-oxobutyric acid

By appropriate application of the procedures described in Example 4 above, 4-[3,5-dichloro-4-(5-bromo-6-hydroxynaphthyl)-phenyl]-4-amino-4-oxobutyric acid (17 mg, 31%) was synthesized from Compound 1f (40 mg, 0.112 mmol). 1H-NMR and mass spec were consistent with the proposed structure.

EXAMPLE 6

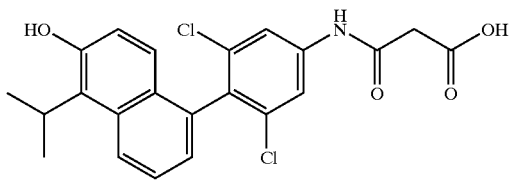

3-[3,5-dichloro-4-[5-(1-methylethyl)-6-hydroxynaphthyl]-phenyl]-3-amino-3-oxopropanoic acid Compound 6a:

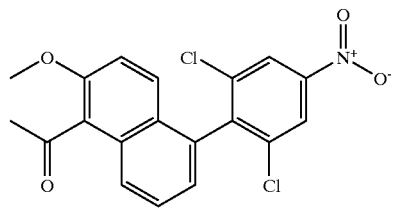

Compound 1d (282 mg, 0.81 mmol) and acetic anhydride (244 mg, 2.4 mmol) were dissolved in anhyd dichloromethane (10 mL) under a blanket of argon and cooled to −78° C. Boron trifluoride dimethyl sulfide complex (311 mg, 2.4 mmol) was added dropwise. The reaction was stirred at −78° C. for 10 min then warmed to room temperature for 6 hrs. Compound 6a (243 mg, 77%) was isolated by silica gel chromatography (30 g silica gel, elute with 5% ethyl acetate in hexanes). 1H-NMR was consistent with the proposed structure.

Compound 6b:

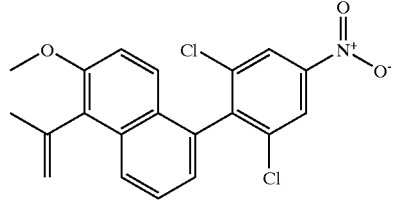

Nysted reagent (927 μL of a 20% w/w solution in THF, 216 mg, 0.47 mmol) was suspended in anhyd tetrahydrofuran (2 mL) and cooled to −78° C. A solution of the ketone from 6a (148 mg, 0.38 mmol) in anhyd dichloromethane (2 mL) was added over a period of 10–15 min. Titanium tetrachloride (1.0 M in dichloromethane, 380 μL, 0.38 mmol) was added dropwise. The reaction was stirred for a further 0.5 hrs. at −78° C., then warmed to room temperature overnight. The reaction was diluted with ethyl acetate, washed with saturated aqueous sodium bicarbonate and brine, dried over anhyd magnesium sulfate, filtered and dried in vacuo. Compound 6b (40 mg, 27%) was isolated by silica gel chromatography (8 g silica gel, elute with 2.5% ethyl acetate in hexanes). 1H-NMR was consistent with the proposed structure.

Compound 6c:

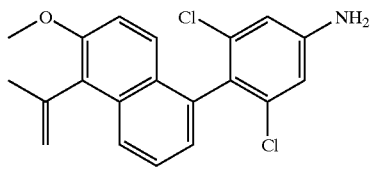

Compound 6b (40 mg, 0.103 mmol) was dissolved in acetic acid (3 mL) and water (0.3 mL). Iron powder (57 mg, 1.0 mmol) was added and the reaction stirred vigorously for 1 h. The reaction was filtered through a pad of celite. The celite was rinsed with ethyl acetate three times. The combined organic layers were washed with water, saturated aqueous sodium bicarbonate and brine, dried over anhyd magnesium sulfate, filtered and evaporated in vacuo to yield 38 mg (99%) of product. 1H-NMR was consistent with the proposed structure.

Compound 6d:

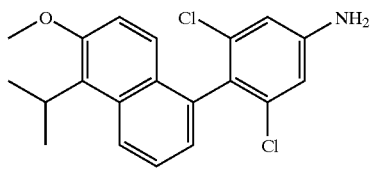

The olefin formed by Compound 6c (36 mg, 0.102 mmol) was dissolved in ethanol (1 mL). Platinum (IV) oxide (25 mg) was added and the reaction rapidly stirred under 1 atmosphere of hydrogen gas. After 2 hrs., the reaction was filtered and dried in vacuo to yield 36 mg (98%) of the title compound. 1H-NMR was consistent with the proposed structure.

Compound 6e:

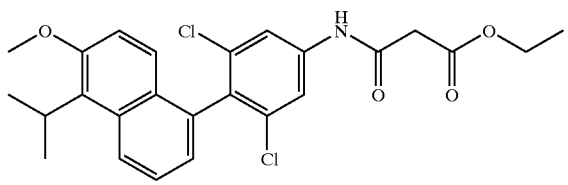

Compound 6d (37 mg, 0.102 mmol) and triethyl amine (12 mg, 0.122 mmol) were dissolved in anhyd dimethyl formamide and cooled to 0° C. Ethyl 3-chloro-3-oxoproprionate (18 mg, 0.122 mmol) was added dropwise. The reaction was warmed to room temperature and stirred overnight. Additional ethyl 3-chloro-3-oxorproprionate (7.5 mg, 0.05 mmol) was added. The reaction was complete after 2 h. The solvent was evaporated in vacuo. The residue was dissolved in ethyl acetate and washed with water and brine, dried over anhyd magnesium sulfate, filtered and evaporated in vacuo to yield 45 mg of crude product. Compound 6e (14 mg, 29%) was isolated by silica gel chromatography (3 g silica gel, elute with 20% ethyl acetate in hexanes). 1H-NMR was consistent with the proposed structure.

Compound 6e (14 mg, 0.03 mmol) was dissolved in anhyd dichloromethane (300 μL) and cooled to −78° C. under a blanket of argon. Boron tribromide (74 mg, 0.3 mmol) was added dropwise. The reaction was stirred at −78° C. for 15 min then warmed to 0° C. for 2 hrs. The excess boron tribromide was quenched by pouring the reaction mixture into a flask containing a rapidly stirring mixture of ethyl acetate and aqueous ammonium chloride. The organic layer was separated and washed with brine, dried over anhyd magnesium sulfate, filtered and evaporated in vacuo. The residue was dissolved in methanol (1 mL) and treated with 1 N sodium hydroxide (0.1 mL) at room temperature for 2 hrs. The methanol was removed in vacuo. The residue was diluted with water, acidified to a pH of 1 with 1 N hydrochloric acid and extracted with ethyl acetate. The combined extracts were washed with brine, dried over anhyd magnesium sulfate, filtered and evaporated in vacuo to yield 10 mg (78%) of the title product of Example 6 as a yellow glass. 1H-NMR and mass spec were consistent with the proposed structure.

EXAMPLE 7

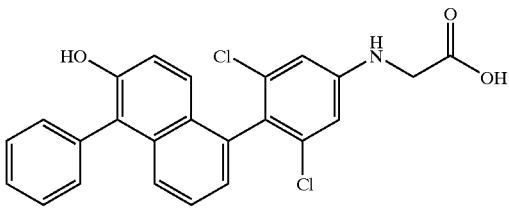

N-[3,5-dichloro-4-(5-phenyl-6-hydroxynaphthyl)-phenyl]-glycine

Compound 7a:

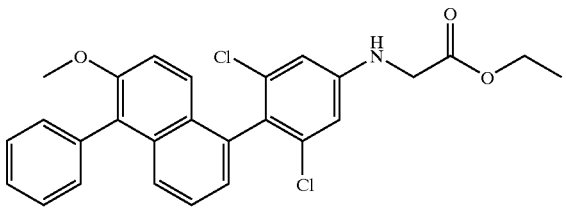

Compound 3a (26 mg, 0.054 mmol), phenylboronic acid (20 mg, 0.16 mmol) and sodium carbonate (18 mg, 0.16 mmol) were dissolved in dimethoxyethane (300 μL) and water (50 μL). The solution was degassed by nitrogen sparge for 10 min. Tetrakis(triphenylphosphine) palladium (0) (18 mg, 0.015 mmol) was added and the reaction mixture heated to 80° C. for 4 h. The reaction mixture was cooled to rt, diluted with water and extracted with ethyl acetate. The combined extracts were washed with brine, dried over anhyd sodium sulfate and evaporated in vacuo. Compound 7a (12 mg, 47%) was isolated by preparative thin layer chromatography (elute with 40% ethyl acetate in hexanes). 1H-NMR was consistent with the proposed structure.

The product from 7a (12 mg, 0.026 mmol)) was deprotected using the protocol described for compound 1h. The title compound of Example 7 (11 mg, 98%) was isolated by preparative high performance reverse phase chromatography (YMC ODS 20×100 mm column; buffer A=0.1% TFA in 10% methanol in water, buffer B=0.1% TFA in 90% methanol in water; gradient=50–100% B in 15 min). 1H-NMR and mass spec were consistent with the proposed structure.

EXAMPLE 8

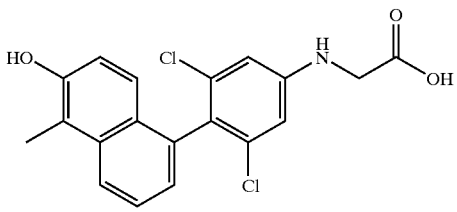

N-[3,5-dichloro-4-(5-methyl-6-hydroxynaphthyl)-phenyl]-glycine

Compound 8a:

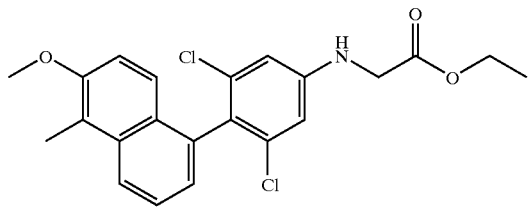

Compound 3a (20 mg, 0.041 mmol), tribasic potassium phoshphate (30 mg, 0.14 mmol), methylboronic acid (15 mg, 0.25 mmol) and 1,1'-bis[diphenylphosphino(ferrocene)]-dichloropalladium(II):dichloromethane 1:1 complex (16 mg, 0.02 mmol) were placed into a pressure tube and dissolved in dioxane. The solution was degassed by nitrogen sparge for 10 min. The tube was flushed with argon, sealed and heated to 110° C. overnight. The reaction was cooled to room temperature, diluted with ethyl acetate, washed with water and brine, dried over anhyd magnesium sulfate and dried in vacuo. Compound 8a (10 mg, 58%) was isolated by preparative thin layer chromatography (elute with 40% ethyl acetate in hexanes). 1H-NMR was consistent with the proposed structure.

The product from 8a (10 mg, 0.024 mmol) was deprotected using the protocol described for compound 1h. The title compound of Example 8 (4.3 mg, 48%) was isolated by preparative high performance reverse phase chromatography (YMC ODS 20×100 mm column; buffer A=0.1% TFA in 10% methanol in water, buffer B=0.1% TFA in 90% methanol in water; gradient=50–100% B in 15 min). 1H-NMR and mass spec were consistent with the proposed structure.

EXAMPLES 9–15

By appropriate application of the procedures described above, Examples 9–15 were prepared.

| Example | $R_1$ | $R_2$ | $R_3$ | $R_4$ |
|---|---|---|---|---|
| 9 | $CH_3$ | Cl | Cl | $NHCOCH_2COOH$ |
| 10 | Br | H | Cl | $CONHCH_2COOH$ |
| 11 | Ph | H | Cl | $CONHCH_2COOH$ |
| 12 | Br | Cl | Cl | $CH_2COOH$ |
| 13 | Br | Cl | Cl | $NH_2$ |
| 14 | Br | H | Cl | $CH_2COOH$ |
| 15 | H | Cl | Cl | $CH_2COOH$ |

What is claimed is:

1. A compound of the formula I:

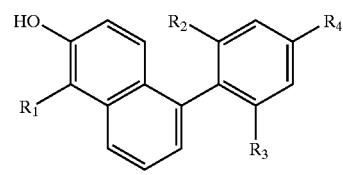

wherein $R_1$ is selected from the group consisting of halogen, trifluoromethyl, aryl, $C_{1-6}$ alkyl and $C_{1-7}$ cycloalkyl, wherein the aryl group may optionally be substituted with one or more functional group selected from the group consisting of hydrogen, halogen, alkyl, haloalkyl, alkoxy, haloalkoxy, alkenyl, trifluoromethyl, trifluoromethoxy, alkynyl, hydroxy, amino, nitro, cyano, aryl, cycloalkyl, heteroaryl, carboxyl or an alkyl ester thereof, and carboxamide;

the $C_{1-6}$ alkyl group may optionally be substituted with one or more substituent selected from the group consisting of alkyl, alkenyl, alkynyl, aryl, cycloalkyl, heteroaryl, hydroxy, cyano, nitro, amino, halogen, carboxyl or an alkyl ester thereof, and carboxamide;

the $C_{1-7}$ cycloalkyl group may optionally be substituted with one or more substituent selected from the group consisting of hydrogen, halogen, alkyl, haloalkyl, alkoxy, haloalkoxy, alkenyl, trifluoromethyl, trifluoromethoxy, alkynyl, hydroxy, amino, nitro, cyano, aryl, cycloalkyl, heteroaryl, carboxyl or an alkyl ester thereof, and carboxamide;

$R_2$ and $R_3$ are each independently selected from the group consisting of hydrogen, halogen, $C_{1-4}$ alkyl and $C_{3-6}$ cycloalkyl, wherein at least one of $R_2$ and $R_3$ is other than hydrogen, and wherein the $C_{1-6}$ alkyl group may optionally be substituted with one or more substituent selected from the group consisting of alkyl, alkenyl, alkynyl, aryl, cycloalkyl, heteroaryl, hydroxy, cyano, nitro, amino, halogen, carboxyl or an alkyl ester thereof, and carboxamide;

the $C_{1-7}$ cycloalkyl group may optionally be substituted with one or more substituent selected from the group consisting of hydrogen, halogen, alkyl, haloalkyl, alkoxy, haloalkoxy, alkenyl, trifluoromethyl, trifluoromethoxy, alkynyl, hydroxy, amino, nitro, cyano, aryl, cycloalkyl, heteroaryl, carboxyl or an alkyl ester thereof, and carboxaide;

$R_4$ is selected from the group consisting of $(CH_2)_nCOOH$, $(CH)_2COOH$, $NHCO(CH_2)_nCOOH$, $CONH(CH_2)_nCOOH$ and $NH(CH_2)_mCOOH$, or esters thereof;

n is an integer from 0 to 4; and m is an integer from 1 to 4, including all stereoisomers thereof, prodrug esters thereof, and pharmaceutically acceptable salts thereof.

2. The compound as defined in claim 1 wherein:

$R_1$ is selected from the group consisting of halogen, $C_{1-3}$ alkyl and aryl wherein;

the $C_{1-3}$ alkyl group may optionally be substituted with one or more substituent selected from the group consisting of alkyl, alkenyl, alkynyl, aryl, cycloalkyl, heteroaryl, hydroxyl, cyano, nitro, amino, halogen, carboxyl or an alkyl ester thereof, and carboxamide;

the aryl group may optionally be substituted with one or more substituent selected from the group consisting of hydrogen, halogen, alkyl, haloalkyl, alkoxy, haloalkoxy, alkenyl, trifluoromethyl, trifluoromethoxy, alkynyl, hydroxy, amino, nitro, cyano, aryl, cycloalkyl, heteroaryl, carboxyl or an alkyl ester thereof, and carboxamide;

$R_2$ and $R_3$ are each independently hydrogen or chloro, wherein at least one of $R_2$ and $R_3$ is chloro;

$R_4$ is selected from the group consisting of $NHCO(CH_2)_n COOH$, $NH(CH_2)_m COOH$, $CONHCH_2COOH$ and $CH_2COOH$;

n is an integer from 0 to 1; and m is an integer from 1 to 2.

3. The compound as defined in claim 1 wherein $R_1$ is bromo or substituted or unsubstituted $C_{1-3}$ alkyl;

$R_2$ and $R_3$ are chloro;

$R_4$ is $NHCO(CH_2)_n COOH$ or $NH(CH_2)_m COOH$;

n is an integer from 0 to 1; and m is an integer from 1 to 2.

4. The compound as defined in claim 1 having the structure:

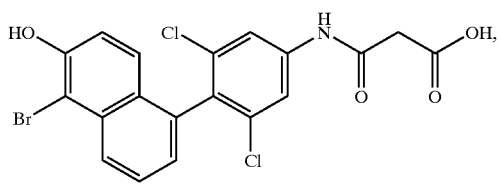

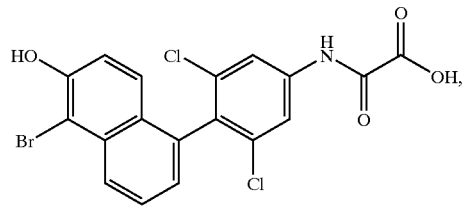

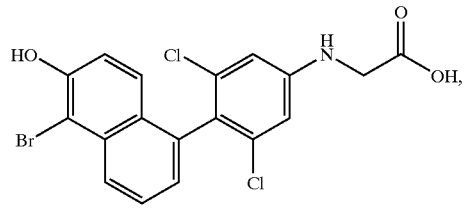

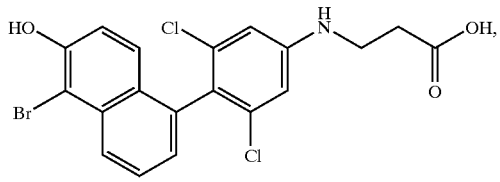

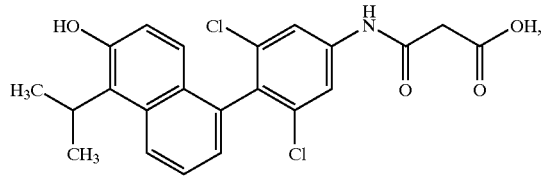

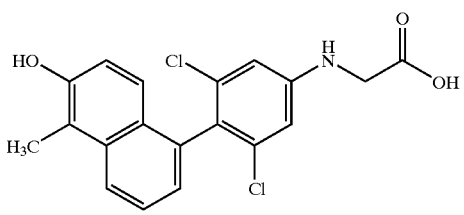

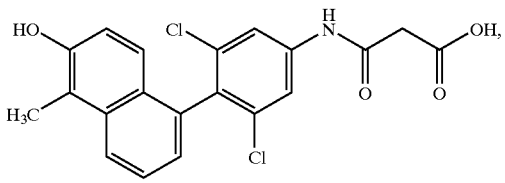

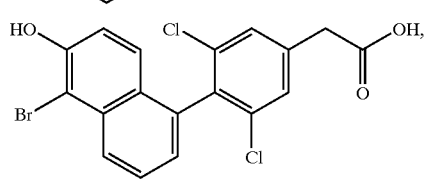

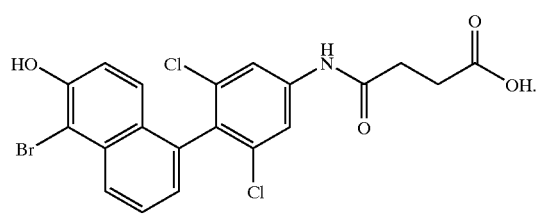

5. The compound as defined in claim 1 having the structure:

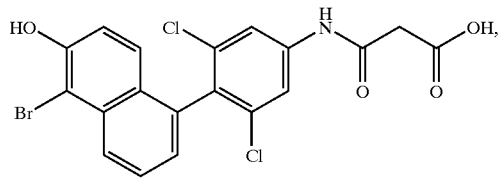

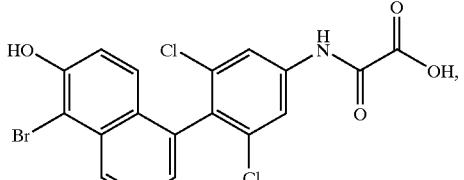

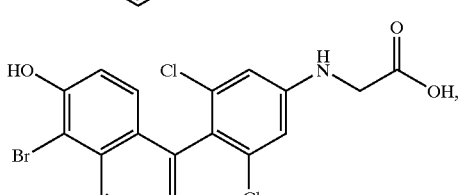

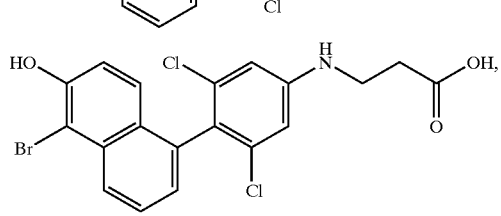

-continued
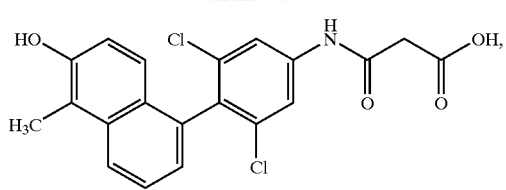
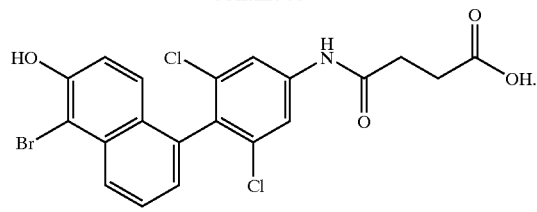
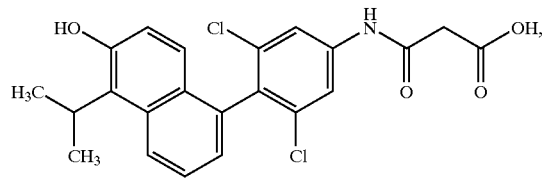
6. A pharmaceutical composition comprising a compound as defined in claim 1 and a pharmaceutically acceptable carrier therefor.
7. A pharmaceutical composition which functions as a selective agonist of the thyroid hormone receptor-beta comprising a compound as defined in claim 1.
* * * * *

UNITED STATES PATENT AND TRADEMARK OFFICE
CERTIFICATE OF CORRECTION

PATENT NO. : 6,831,102 B2
DATED : December 14, 2004
INVENTOR(S) : Jon J. Hangeland It is certified that error appears in the above-identified patent and that said Letters Patent is hereby corrected as shown below:

Column 30,
Line 18, "more functional group selected from the group consist-" should read
-- more substituent selected from the group consist --
Lines 29 and 45, "$C_{1-7}$" should read -- $C_{3-7}$ --

Signed and Sealed this

Twelfth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,831,102 B2
DATED : December 14, 2004
INVENTOR(S) : Jon J. Hangeland It is certified that error appears in the above-identified patent and that said Letters Patent is hereby corrected as shown below:

Column 8,
Line 51, "R=RI=C", please replace with -- $R=R^I=C$ --
Line 63, "The B group in formulas 2 and 3 represent", please replace with
-- The B group formula 2 represents --

Column 11,
Line 2, "bromine at RI", please replace with -- bromine at $R_1$ --
Line 51, "Example 5", please replace with -- Example 6 --

Signed and Sealed this

Nineteenth Day of July, 2005

JON W. DUDAS
*Director of the United States Patent and Trademark Office*